(12) United States Patent
Boehm

(10) Patent No.: US 7,374,006 B2
(45) Date of Patent: May 20, 2008

(54) METHOD AND DEVICE FOR DETERMINING THE ROADWAY CONDITION

(75) Inventor: Konrad Boehm, Blaustein (DE)

(73) Assignee: Daimler AG, Stuttgart (DE)

( * ) Notice: Subject to any disclaimer, the term of this patent is extended or adjusted under 35 U.S.C. 154(b) by 653 days.

(21) Appl. No.: 10/935,438

(22) Filed: Sep. 7, 2004

(65) Prior Publication Data

US 2005/0087377 A1    Apr. 28, 2005

(30) Foreign Application Priority Data

Sep. 8, 2003   (DE) ............................. 103 41 685
Oct. 23, 2003  (DE) ............................. 103 49 515

(51) Int. Cl.
  *B62D 1/24*    (2006.01)
(52) U.S. Cl. .................. 180/167; 701/80; 340/146.2; 340/500; 340/540; 340/580; 324/637; 324/642
(58) Field of Classification Search ............... 324/643, 324/76.11; 701/80; 180/167, 169; 340/146.2, 340/500, 540, 580
See application file for complete search history.

(56) References Cited

U.S. PATENT DOCUMENTS

| | | | | |
|---|---|---|---|---|
| 3,351,870 | A * | 11/1967 | Goldsmith et al. ............ | 372/81 |
| 3,402,367 | A * | 9/1968 | Kobayashi ................... | 372/88 |
| 3,543,179 | A * | 11/1970 | Wilson ........................ | 372/58 |
| 3,721,915 | A * | 3/1973 | Reilly .......................... | 372/74 |
| 5,497,100 | A | 3/1996 | Reiser et al. ................ | 324/643 |
| 6,489,915 | B1 | 12/2002 | Lines et al. .................... | 342/26 |
| 2003/0206295 | A1 * | 11/2003 | Vaez-Iravani et al. ... | 356/237.2 |
| 2005/0174568 | A1 * | 8/2005 | Vaez-Iravani et al. ... | 356/237.2 |

FOREIGN PATENT DOCUMENTS

| | | |
|---|---|---|
| DE | 29 12 645 | 10/1980 |
| DE | 38 29 008 | 3/1989 |
| DE | 37 38 221 | * 6/1989 |
| DE | 197 18 623 | 11/1998 |
| DE | 198 16 004 | * 10/1999 |
| EP | 0 875 750 | 11/1998 |
| EP | PCT/EP88/00950 | * 5/1999 |

OTHER PUBLICATIONS

I. J. Padaratz et al., Coupling effects of radar antennae on concrete, in NDT-CE'97 1997, vol. 1 pp. 237-245, cited by another.*
Interaction of electromagnetic waves with some natural surfaces, Peake, W.; Antennas and Propagation, IEEE Transactions on legacy, pre—1988, vol. 7, Issue 5, Dec. 1959 pp. 324-329.*

(Continued)

*Primary Examiner*—Cuong Nguyen
(74) *Attorney, Agent, or Firm*—Davidson, Davidson & Kappel, LLC

(57) ABSTRACT

A method and a device for determining the condition of roadway surfaces includes transmitting electromagnetic radiation at at least two different frequencies in the GHz range, reflecting and/or scattering the electromagnetic radiation by the roadway surface and subsequently receiving the electromagnetic radiation at the at least two frequencies. The condition of the roadway surface is determined on the basis of a comparison of the radiation intensities received at the different frequencies.

17 Claims, 2 Drawing Sheets

OTHER PUBLICATIONS

Simultaneous detection of lane and pavement boundaries using model-based multisensor fusion, Ma, B.; Lakshmanan, S.; Hero, A.O., III; Intelligent Transportation Systems, IEEE Transactions on, vol. 1, Issue 3, Sep. 2000 pp. 135-147 Digital Object Identifier 10.1109/6979.892150.*

Understanding the relationships between radar response patterns and the bio- and geophysical parameters of urban areas☐☐Zong-Guo Xia; Henderson, F.M.; Geoscience and Remote Sensing, IEEE Transactions on, vol. 35, Issue 1, Jan. 1997 pp. 93-101.*

Modeling and measurements of scattering from road surfaces at millimeter-wave frequencies, Sarabandi, K.; Li, E.S.; Nashashibi, A.; Antennas and Propagation, IEEE Transactions on, vol. 45, Issue 11, Nov. 1997 pp. 1679-1688 Digital Object Identifier 10.1109/8.650080.*

1997 Index IEEE Transactions on Antennas and Propagation vol. 45, Antennas and Propagation, IEEE Transactions on vol. 45, Issue 12, Dec. 1997 pp. 1-36, Digital Object Identifier 10.1109/TAP.1997.650215.*

Forecast: a neural system for diagnosis and control of highway surfaces, Luchetta, A.; Manetti, S.; Francini, F.; Intelligent Systems and Their Applications, IEEE [see also IEEE Intelligent Systems], vol. 13, Issue 3, May-Jun. 1998 pp. 20-26, Digital Object Identifier 10.1109/5254-683177.*

Low grazing incidence millimeter-wave scattering models and measurements for various road surfaces, Li, E.S.; Sarabandi, K.; Antennas and Propagation, IEEE Transactions on, vol. 47, Issue 5, May 1999 pp. 851-861, Digital Object Identifier 10.1109/8.774140.*

Polarimetric characterization of debris and faults in the highway environment at millimeter-wave frequencies, Sarabandi, K.; Li, E.S.; Antennas and Propagation, IEEE Transactions on, vol. 48, Issue 11, Nov. 2000 pp. 1756-1768 Digital Object Identifier 10.1109/8.900234.*

An image processing method to detect road surface condition using optical spatial frequency, Fukui, H.; Takagi, J.; Murata, Y.; Takeuchi, M.; Intelligent Transportation System, 1997. ITSC 97. IEEE Conference on, Nov. 9-12, 1997 pp. 1005-1009 Digital Object Identifier 10.1109/ITSC.1997.660611.*

Physical optics models for the backscatter response of road-surface faults and roadside pebbles at millimeter-wave frequencies Li, E.S.; Antennas and Propagation, IEEE Transactions on, vol. 51, Issue 10, Part 2, Oct. 2003 pp. 2862-2868 Digital Object Identifier 10.1109/TAP.2003.818004.*

Understanding the relationships between radar response patterns and the bio- and geophysical parameters of urban areas Zong-Guo Xia; Henderson, F.M.; Geoscience and Remote Sensing, IEEE Transactions on, vol. 35, Issue 1, Jan. 1997 pp. 93-101, Digital Object Identifier 10.1109/36.551938.*

Amplitude distribution of composite terrain radar clutter and the κ-Distribution, Jen Jao; Antennas and Propagation, IEEE Transactions on [legacy, pre—1988], vol. 32, Issue 10, Oct. 1984 pp. 1049-1062.*

Proceedings of the 1997 IEEE National Radar Conference, Radar Conference, 1997., IEEE National, May 13-15, 1997 Digital Object Identifier 10.1109/NRC.1997.588309.*

S. Hertl et al., Contactless determination of the properties of water films on roads, J. Phys. E: Sci Instrum. 21 (1988) 955—958; XP-002309983.

Search Report of Corresponding EP 04 02 0755 and brief translation thereof.

* cited by examiner

METHOD AND DEVICE FOR DETERMINING THE ROADWAY CONDITION

Priority is claimed to German Patent Application No. DE 103 416 85.4, filed on Sep. 8, 2003, and to German Patent Application No. DE 103 49 515.0, filed on Oct. 23, 2003, both of which are incorporated by reference herein.

The present invention relates to a method and a device for determining the roadway condition for vehicles, in particular for motor vehicles.

BACKGROUND

A prerequisite for the safe forward movement of a vehicle is the reliable optimum adherence of the vehicle tires to the roadway.

Suddenly appearing slippery or wet surfaces affect this adherence considerably and are therefore frequent causes of accidents, often with grave consequences. The specific problem here is that the vehicle's driver often does not recognize the slippery or wet surface or recognizes it too late, and therefore quickly loses control of the vehicle.

To overcome this dangerous situation, different systems have been proposed which support the driver in estimating the condition of the roadway surface and/or initiate automatic accident prevention measures.

Thus, for example, German Patent Application DE 197 18 623 A1 describes a system in which the condition of the roadway surface is determined using radar beams. However, the problem with this approach is that the known method does not provide clear results, and does not ensure reliable determination of the roadway condition.

Another approach to the above-mentioned problem is to draw conclusions regarding the condition of the roadway surface, in particular the coefficient of friction between tires and roadway surface, on the basis of the deformation of the tire profile as the tire rolls on the roadway. To do so, however, a certain number of sensors must be installed in the tires, which raises considerable implementation problems due to the specific installation site (wearing parts, high accelerations, difficult contacting for signal transmission).

In German Patent Application DE 29 12 645 A1, a device for warning of a slippery surface is proposed, in which the condition of the roadway surface is determined using reflected electromagnetic waves at different frequencies. The device disclosed in the cited document, however, has considerable disadvantages. For example, the device described therein exhibits increased susceptibility to changing propagation conditions of the used electromagnetic signals. Changes in the propagation conditions may be caused by geometric changes, for example, short-term changes in the distance of the sensors from the roadway surface.

SUMMARY OF THE INVENTION

An object of the present invention is to provide a device and a method which ensure reliable, robust, and cost-effective determination of the condition of a roadway surface.

The present invention provides a method for determining the condition of roadway surfaces, in which electromagnetic radiation having a frequency in the GHz range being transmitted at at least two different frequencies, reflected and/or scattered by the roadway surface and subsequently received, and wherein the condition of the roadway surface is determined on the basis of a comparison of the radiation intensities received at different frequencies. The present invention also provides a device for determining the condition of roadway surfaces having a transmitting unit and a receiving unit for transmitting and receiving, respectively, electromagnetic radiation at at least two different frequency ranges in the GHz range, as well as a control unit and an analyzer unit, wherein the analyzer unit is suitable for determining the condition of the roadway surface via a comparison of the received intensities.

Electromagnetic radiation at different frequencies in the GHz range is utilized in the method according to the present invention for determining the condition of a roadway surface. This radiation is emitted in the direction of the roadway surface by a transmitting unit preferably mounted on the bottom of the vehicle and is received by a receiving unit after reflection or scattering on the roadway surface. The intensities of the electromagnetic radiation at different frequencies received by the receiving unit are then determined on the basis of the received signal strength and compared in a comparator unit.

The electromagnetic radiation at different frequencies may be emitted and received either simultaneously or sequentially.

The comparison of the intensities of the received radiation has the advantage that interfering effects and thus misinterpretations of the measurement results may be largely suppressed. Considering a single signal strength, for example, at one frequency, would be highly susceptible to interference occurring on the signal path from the transmitter unit to the roadway surface and back to the receiving unit.

For example, a suddenly occurring dirt accumulation on a transmitting or receiving antenna would immediately reduce the level of the received signal, which would result in erroneous determination of the roadway surface condition. In contrast, the method according to the present invention effectively prevents this effect, because such a dirt accumulation affects the signal level of all received signals and the effect is suppressed in the comparison of the received intensities.

BRIEF DESCRIPTION OF THE DRAWINGS

The present invention if described in further detail below with reference to the drawings, in which.

DETAILED DESCRIPTION

Figure 1:
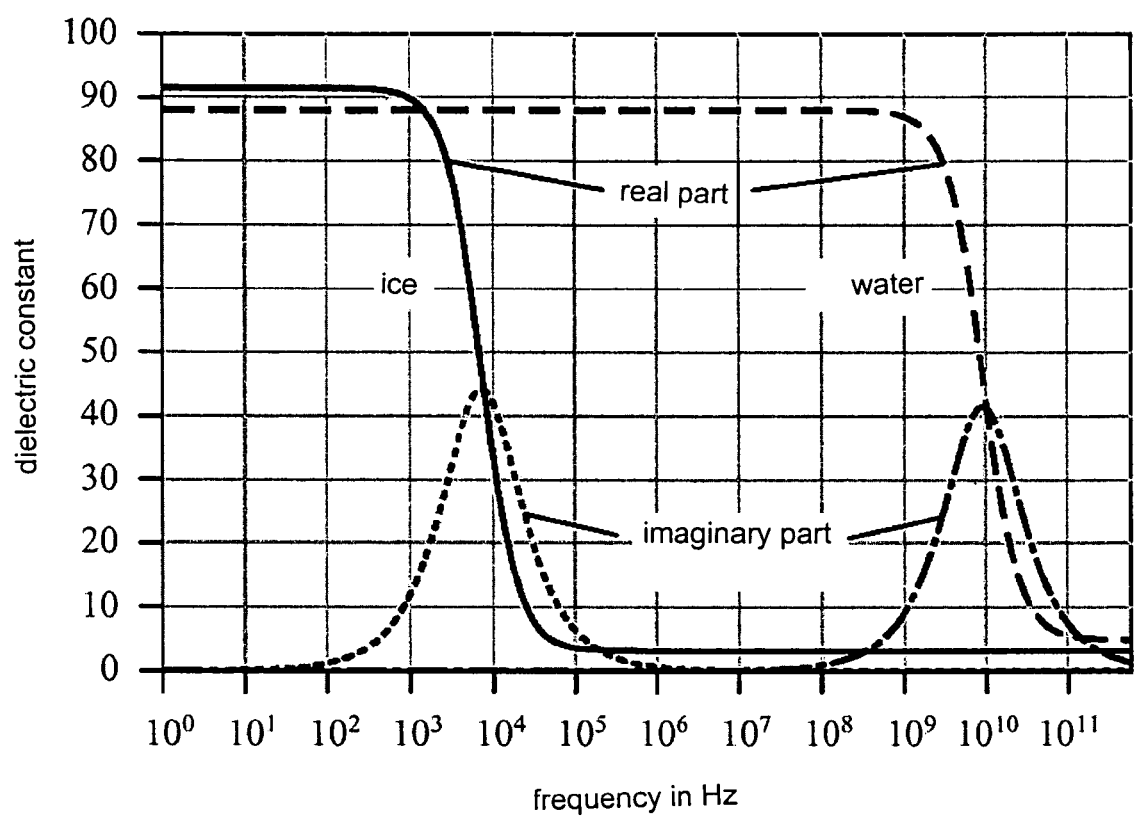
FIG. 1 is a chart showing the curve of the complex dielectric constant for water and ice.

It has proven to be particularly advantageous that the presence of water on the roadway surface is inferred from the comparison of the received intensities. The method according to the present invention is therefore particularly suitable for detecting water on the roadway surface, because water has specific dielectric properties just in the GHz range. Water molecules have a permanent electric dipole moment and may therefore be excited to rotate by alternating electrical fields. This effect is known as orientation polarization. These properties of water result from the fact that the complex dielectric constant of water at low frequencies up to approximately 100 MHz has a large real part and a small imaginary part. Above the relaxation frequency range, which is at approximately 10 GHz, the molecules are no longer able to follow the excitation field; the real part of the dielectric constant, which determines the refraction index, drops considerably in this range, while the imaginary part, which is, as known, related to the absorption coefficient, has a maximum here. The exact curve of the complex dielectric constant of water and ice is shown in FIG. 1.

Due to the pronounced change in the refraction index of water in the above-described frequency range, the reflectivity of a water surface changes drastically in that frequency range. Thus, when selecting electromagnetic radiation from that frequency range, it is to be expected that the intensities reflected by the water surface clearly differ, while in the absence of water, no major difference in the intensities reflected from an asphalt surface, for example, is to be expected.

The method according to the present invention thus permits a reliable determination to be made, on the basis of the specific dielectric properties of water, of whether a roadway surface is wet or dry. Since this determination is performed predominantly on the basis of the reflection properties of the surface being considered and thus on the basis of the properties of a boundary surface, the thickness of the water film on the roadway surface is largely irrelevant for determining the roadway condition; a reliable distinction may thus be made between a wet and a dry roadway surface.

Figure 2:
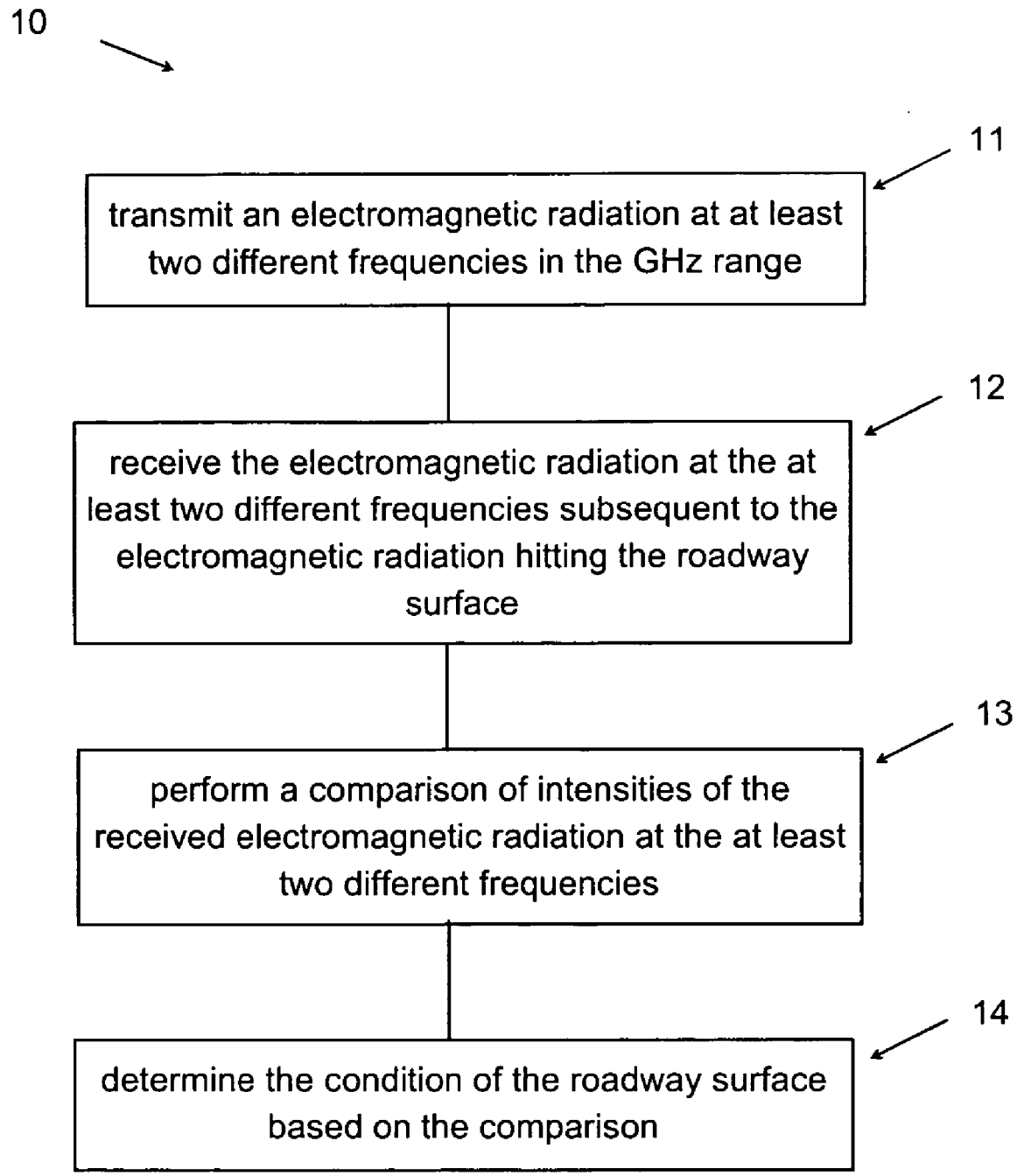
FIG. 2 is a flow chart illustrating a method for determining a condition of a roadway surface according to the present invention.

As shown in FIG. 2, the present invention provides a method 10 for determining a condition of a roadway surface. In a first step, an electromagnetic radiation is transmitted at at least two different frequencies in the GHz range. See block 11. In a second step, the electromagnetic radiation is received at the at least two different frequencies subsequent to the electromagnetic radiation hitting the roadway surface. See block 12. A comparison of intensities of the received electromagnetic radiation at the at least two different frequencies is performed. See block 13. Based on the comparison, the condition of the roadway surface is determined. See block 14.

In a particularly advantageous embodiment of the present invention, the received intensities from the frequency ranges of approximately 2.4 GHz and approximately 5.8 GHz are compared. The particular advantage of this selection is that the real part of the dielectric constant of water changes in a particularly pronounced manner in this frequency range and thus the comparison of the received intensities provides an unambiguous result. Moreover, the two frequency bands at 2.4 GHz and 5.8 GHz are known as ISM (industrial, scientific and medical) bands and are thus permit-free, so that electromagnetic transmissions in these frequency ranges are not subject to any legal restrictions; thus there is no formal impediment to the implementation of the method according to the present invention. This special selection of frequency ranges therefore permits an efficient method for determining the condition of a roadway surface to be used without a costly process to obtain permissions.

In a preferred embodiment of the method according to the present invention, the transmitted electromagnetic radiation is narrow-band signals at at least two different frequencies. The use of narrow-band signals makes it possible to operate with a high spectral power density in the relevant frequency ranges, which considerably facilitates the reception of the signals reflected or scattered by the roadway surface. In particular, in selecting the above-mentioned frequency bands for the mid-frequency of the signals used, any possible interference in other frequency ranges is also reduced.

Conversely, it is also conceivable that the transmitted electromagnetic radiation is an extremely broadband signal, in particular a UWB (ultra-wide band) signal. UWB signals are characterized by their extremely high bandwidth with a much lower spectral power density at the same time. In practice, short, steep-edged pulses are used for transmitting a UWB signal. A Fourier transformation of the received signal provides the full spectrum, on the basis of which the condition of the roadway surface may be determined via the above-described comparison of the intensities of the received radiation in the relevant spectral ranges.

The particular advantage of this variant of the present invention is that, due to the low spectral power density of the UWB signals, third-party interference is minimized and the extreme width of the analyzed frequency range opens the possibility of a spectroscopic examination of the received signals.

In a particularly advantageous embodiment of the present invention, the intensities are compared by forming the quotient of radiation intensities received at two different frequencies. In the absence of water, it is to be expected that the intensities of the signals reflected and/or scattered in the different frequency ranges do not substantially differ. Consequently, a certain value R1 is to be expected as the result of quotient formation in this case. If there is water on the roadway surface, the transmitted electromagnetic radiation is reflected with different intensities depending on the frequency. The quotient formation therefore yields a value R2, which clearly differs from the above value, and which may be used to distinguish between a dry and a wet roadway surface.

The real and imaginary parts of the reflected and/or scattered signal may be determined separately using quadrature signal processing.

By analyzing the real and imaginary parts at two different frequencies, four different values of the quotient may be determined.

This measure considerably increases the reliability and unambiguousness in determining the roadway condition.

The results of the method according to the present invention may be further improved by using radiation which is polarized perpendicularly to the plane of incidence. The plane of incidence is defined by the incident and reflected beam and is thus perpendicular to the boundary surface. Radiation polarized perpendicularly to the plane of incidence exhibits the characteristic that it is reflected to a higher degree at a boundary surface when passing from an optically thinner to an optically denser medium than electromagnetic radiation, for example, which is polarized in parallel or unpolarized. This fact is easily derived from Fresnel's formulas which provide the relationship between polarization, angle of incidence, and reflected intensity at a boundary surface in particular. Making use of this fact, it is thus possible to increase the intensity of the radiation reflected by the roadway surface simply by selecting polarization and thus further increasing the reliability and accuracy of the method according to the present invention.

The method according to the present invention may also be used for adapting control parameters for one or more driver assistance systems when water is detected on the roadway surface. The effectiveness of driver assistance systems, such as electronic stability program ESP, depends substantially on the amount of available information regarding the roadway condition. Although it is possible to obtain this information from the vehicle dynamics, this procedure has the disadvantage that the thus obtained information regarding the condition of the roadway surface is not available until it has already affected the vehicle dynamics, i.e., for example, aquaplaning or slipping has occurred. Here the results of the method according to the present invention may advantageously be used for optimizing the control parameters for driver assistance systems even before critical driving situations occur, thereby gaining an important time advantage and increasing driving safety.

An exemplary device for implementing the above-described method shows a transmitting unit and a receiving unit for transmitting and receiving, respectively, electromagnetic radiation at at least two different frequencies in the GHz range, as well as a control unit and an analyzer unit. The analyzer unit is suitable for determining the condition of the roadway surface via a comparison of the intensities of the received electromagnetic radiation. The transmitting unit has, for example, a signal generator and a transmitting antenna connected thereto, via which electromagnetic radiation of the desired frequency range and desired intensity may be emitted. The polarization of the emitted radiation is essentially determined by the spatial orientation of the transmitting antenna. Dipole antennas, dielectric antennas, leak waveguides, open waveguides (slotted coaxial conductors, Harms Goubau lines, etc.) and the like may be used as transmitting antennas. After reflection on the roadway surface, part of the electromagnetic radiation is received by a receiving antenna and supplied to an analyzer unit. The transmitting antenna may also be used in this case as the receiving antenna given suitable activation, e.g., in pulsed-mode operation. Once the signal has been received, the analyzer unit performs an analysis, for example, by forming the quotient of the intensities of the signals received in different frequency ranges and delivers a statement regarding the presence of water on the roadway surface as a result.

The above-described device and the above-described method provide a compact, robust, and reliable system for roadway condition recognition at a low hardware expense, thus increasing highway safety.

What is claimed is:

1. A method for determining a condition of a roadway surface, the method comprising:
    transmitting an electromagnetic radiation at at least two different frequencies in a GHz range;
    receiving the electromagnetic radiation at the at least two different frequencies subsequent to the electromagnetic radiation hitting the roadway surface;
    performing a comparison of intensities of the received electromagnetic radiation at the at least two different frequencies; and
    determining the condition of the roadway surface based on the comparison.

2. The method as recited in claim 1, wherein the determining of the condition includes concluding whether water is present on the roadway surface.

3. The method as recited in claim 1, wherein the at least two frequencies includes a first frequency of approximately 2.4 GHz and a second frequency of approximately 5.8 GHz.

4. The method as recited in claim 1, wherein the electromagnetic radiation includes narrow-band signals at the at least two different frequencies.

5. The method as recited in claim 3, wherein the electromagnetic radiation includes narrow-band signals at the at least two different frequencies.

6. The method as recited in claim 1, wherein the electromagnetic radiation includes a broadband signal.

7. The method as recited in claim 6, wherein the broadband signal includes a UWB signal.

8. The method as recited in claim 3, wherein the electromagnetic radiation includes a broadband signal.

9. The method as recited in claim 8, wherein the broadband signal includes a UWB signal.

10. The method as recited in claim 1, wherein the performing of the comparison includes forming a quotient using the intensities at two of the at least two different frequencies.

11. The method as recited in claim 4, wherein the performing of the comparison includes forming a quotient using the intensities at two of the at least two different frequencies.

12. The method as recited in claim 5, wherein the performing of the comparison includes forming a quotient using the intensities at two of the at least two different frequencies.

13. The method as recited in claim 10, further comprising determining a real and an imaginary part of the received electromagnetic radiation.

14. The method as recited in claim 11, further comprising determining a real and an imaginary part of the received electromagnetic radiation.

15. The method as recited in claim 12, further comprising determining a real and an imaginary part of the received electromagnetic radiation.

16. The method as recited in claim 1, wherein the electromagnetic radiation is polarized perpendicularly to a plane of incidence.

17. The method as recited in claim 2, further comprising adjusting at least one control parameter of at least one driver assistance system when the presence of water on the roadway surface is concluded.

* * * * *